United States Patent [19]
Stevenson et al.

[11] Patent Number: 5,869,748
[45] Date of Patent: Feb. 9, 1999

[54] ACOUSTIC MONITOR ASSEMBLY

[75] Inventors: Adrian Carl Stevenson, Cambridge, Great Britain; Robert Steven Marks, Rehovot, Israel

[73] Assignee: Biosensing Technologies Limited, Beer-Sheva, Israel

[21] Appl. No.: 756,217

[22] Filed: Nov. 25, 1996

Related U.S. Application Data

[63] Continuation of PCT/GB95/01207, May 24, 1995.

[30] Foreign Application Priority Data

May 25, 1994 [GB] United Kingdom .................. 9410426

[51] Int. Cl.[6] .......................... B01F 15/02; G01N 33/487; G01N 9/00; G01N 29/20
[52] U.S. Cl. .................... 73/53.01; 73/61.75; 73/863.22; 73/579; 73/643; 324/204; 324/239; 435/39; 435/291
[58] Field of Search ............................... 73/53.01, 61.75, 73/61.76, 579, 863.22, 643; 324/204, 239; 435/39, 291

[56] References Cited

U.S. PATENT DOCUMENTS

| | | | |
|---|---|---|---|
| 3,774,717 | 11/1973 | Chodorow | 181/0.5 NP |
| 3,816,773 | 6/1974 | Baldwin et al. | 310/8.1 |
| 3,906,780 | 9/1975 | Baldwin | 73/61 R |
| 4,522,501 | 6/1985 | Shannon | 366/142 |
| 4,651,092 | 3/1987 | Brunsch et al. | 324/204 |
| 4,779,451 | 10/1988 | Ezawa et al. | 73/53 |
| 4,848,139 | 7/1989 | Blake-Coleman et al. | 73/61 R |
| 4,909,081 | 3/1990 | Kulczyk et al. | 73/597 |
| 5,290,589 | 3/1994 | Clough et al. | 427/126.3 |
| 5,293,773 | 3/1994 | Babchin et al. | 73/64.48 |
| 5,333,502 | 8/1994 | Clark, Jr. et al. | 73/623 |
| 5,574,363 | 11/1996 | Jagielinski | 324/204 |
| 5,608,164 | 3/1997 | MacLauchlan | 73/599 |

FOREIGN PATENT DOCUMENTS

| | | |
|---|---|---|
| A 0 453 820 | 3/1991 | European Pat. Off. . |
| A 045 613 | 4/1991 | European Pat. Off. . |
| WO A 92/10 743 | 12/1991 | WIPO . |

*Primary Examiner*—Hezron E. Williams
*Assistant Examiner*—J. David Wiggins
*Attorney, Agent, or Firm*—Richard W. Hanes

[57] ABSTRACT

An acoustic monitor assembly for monitoring the particulate content of a liquid, comprising, a body having an electrically conductive portion, the body contacting a liquid whose content is to be monitored in use, a magnetic field generator for generating a magnetic field to which the electrically conductive portion of the body is exposed, the magnetic field generator being positioned such that magnetic particulates in the liquid are drawn on to said body, and a signal generator for inducing eddy currents which oscillate at an acoustic frequency in the electrically conductive portion of the body and in response to which the body is caused to vibrate, and a monitoring for observing the vibration condition of the body so as to provide an indication of the content of said particulates which are drawn onto the body in the liquid.

18 Claims, 3 Drawing Sheets

ACOUSTIC MONITOR ASSEMBLY

CROSS-REFERENCE TO RELATED APPLICATIONS

This is a continuation of International Application PCT/GB95/01207, with an international filing date of May 24, 1995, now abandoned.

BACKGROUND OF THE INVENTION

The invention relates to an acoustic monitor assembly particularly for use in a biosensor. Many different microbial cells are present throughout the environment, however it is often an onerous task to find out exactly where they are located and how many are present. Unfortunately, no handheld instrument can provide this information even though exposure to certain microbial cells can have debilitating or fatal consequences. Because of these unsatisfactory consequences, there has arisen a strong interest in the monitoring of clinical fluids such as serum, saliva, urine and stools. In addition, the screening of drinking water contaminated with vibrio cholerae, cryptosporidium, total coliforms, legionella, Giardia and heterotrophic bacteria is also important.

Because any screening procedure has to allow for many different types of cells, as well as a great numbers of samples, the favored monitoring/screening approach would have to supply the answer quickly and at minimum cost. Therefore, the ideal candidate, based on current technology would be a synthesis between biological and electronic components, known more generally as a biosensor. Biosensors combine today's modern electronics with a very thin layer of antibodies, which react and adhere to the antigen, in this case particular epitope regions of the microbe cell surface. This adherent process localizes the cells where they can be detected with interrogating beams of light or sound. Unfortunately, the microbial cell counting problem, as described, has not yet yielded to the formidable biosensor revolution. Instead, there is a development restriction that is linked to biosensor systems becoming too complex and costly, betraying the original simplicity of the concept. Therefore, the realization of a new cell counting product requires the solution of two problems. First, there is the development problem, which requires for its solution the instigation of a new biosensor technology that is both cost-effective and simple to apply. The second, and main, problem is to apply the new biosensor technology to the construction of a handheld reader for microbial cell counts. A crucial characteristic required of this reader would be real-time on site monitoring for point-of-care and field diagnostics. currently, no product or technology is available to address these problems.

Conventional biosensors will now be described.

SPR—Surface Plasmon Resonance (Pharmacia)

The SPR approach is relatively insensitive to the presence of cells. It is based on a glass prism coated with a metal layer. Laser light is projected onto the prism and at a particular angle generates what is known as a surface plasmon wave. This occurs at a specific angle whereby what is known as an evanescent wave "leaks" from the surface of the prism. Optical equipment must be configured carefully to record this angle as small fluctuations are crucial to the action of SPR. For example, protein binding to the prism surface elicits a biological perturbation, that modifies the angle. By monitoring the angle, all manner of surface processes can be monitored. Perturbation of the prism surface due to an accumulation of surface bound cells is possible to measure, however this detection scenario is rarely performed with SPR. This choice is a consequence of an interrogating light field interacting with only a small fraction in the cell volume. In addition, costs, specialized materials and the size of the overall system, make the SPR system generally inappropriate for cell measurements. A general sensing system is available from Pharmacia for $120,000.

RN—Resonant Mirror (Fisons)

This approach is slightly more sensitive to cells than the SPR system. Unfortunately, the same limitation of the SPR approach applies to the Resonant Mirror; interrogation of a very small fraction of the cell plus the need for specialized materials. A system supplied by Fisons is available in the $100,000 region.

PW—Piezoelectric Waveguide Devices

Only research prototypes of the piezoelectric waveguide device are available. These work by projecting a high frequency (100 MHz or more) guided acoustic wave along a piezoelectric surface. The received acoustic wave is modified according to any surface viscosity or mass changes. This is a sensitive system so cells binding to the surface would cause an effect, however reported research systems prefer to focus on antibody measurements, demonstrating high sensitivity levels. This acoustic approach is less complicated than the optical approaches, SPR and RN, however cells remain difficult to measure due to limited interactions with the surface acoustic wave. Costs are typically $25,000 for research based systems.

PR—Piezoelectric Resonator Devices (Universal Sensors)

The piezoelectric resonator devices are similar to the piezoelectric waveguide devices, sharing the same basic materials of construction, however they are simpler and operate at a far lower acoustic frequency (10 MHz). There are reports of cell measurements, however an additional step to dry the surface of the device is necessary. More recently, modifications that allow wet cell measurements have been initiated, with some success. Presently, no commercial device is available. Because of the larger interaction of the acoustic wave and the cell, more efficient cell detection is possible with this approach, in addition the system can be made portable. Fluctuations due to surface charge and temperature are the main system limitations. Universal Sensors supply a research system for $6500.

It is clear that although these biosensor technologies achieve useful subnanogram detection levels, substantial adaptations are required to address the demands of the counting problem outlined. In addition, the high costs of purchasing these systems coupled with their physical bulk restricts their application to bench mounted laboratory instrumentation.

OBJECTS OF THE INVENTION

Accordingly, it is the primary object of the present invention to provide apparatus primarily for use in a biosensor for locating and counting microbial cells without the use of piezoelectric materials and where the body of the device can be separate from the remainder of the apparatus, thus avoiding the problems of piezoelectric materials with their requirement for electrical contacts and the like.

Another object of the invention is to provide in a device, of the type described, complete isolation between the chemistry on the one hand and, electrical wires/components on the other hand, adding utility to the device which is normally only associated with optical sensors.

A further object of the invention is to provide such a device which does not respond to liquid conductivity, a function normally identified as a problem for piezoelectric biosensors.

A still further object of the invention is to provide an acoustic monitor assembly for use in a biosensor which can be constructed from easily available, low cost components and can be implemented in a hand-held form.

SUMMARY OF THE INVENTION

In accordance with the present invention, an acoustic monitor assembly comprises a body having an electrically conductive portion, the body contacting a liquid to be monitored in use; a magnetic field generator for generating a magnetic field to which the electrically conductive portion of the body is exposed; means for inducing eddy currents in the electrically conductive portion of the body and in response to which the body is caused to vibrate; and means for monitoring the vibration.

Typically, the electrically conductive portion of the body is metal and in some cases the entire body could be made of metal. However, with a completely metal body, it may be difficult to detect a stable resonant condition and preferably, therefore, the body also includes another mass with a low thermal expansion co-efficient. For example, silica glass is particularly useful. A glass disc and metal coating is disposable but this is completely acceptable in view of its cheapness.

The thickness of the electrically conductive portion will typically be substantially equal to the skin depth of the portion, although certain body sizes may prefer values substantially smaller at one hundredth or one thousandth the skin depth. This ensures that vibrations in the electrically conductive portion are efficiently coupled into the adjacent mass of the body.

The magnetic field generator typically comprises a permanent magnet but an electromagnet could also be used. A field strength of about 1 Tesla is usually suitable.

The inducing means typically comprises an electrical circuit and means for passing a current through the circuit. For example, the circuit could include a coil.

In order to induce eddy currents, the magnetic field from the magnetic field generator and/or the electromagnetic field generated by the inducing means must be varied. Preferably, therefore, the means for passing an electrical current through the circuit generates an oscillating current.

In the preferred example, the means for generating an oscillating current includes means for varying the oscillation frequency.

In some applications, the assembly will be used to monitor whether or not there is a change in the resonant condition of the body but in other cases it may be necessary to monitor the degree of change. To that end, the means for oscillating the current is preferably responsive to the monitoring means to vary the frequency to maintain the resonant condition.

The monitoring means can take a variety of forms and for example could comprise an optical detector. Preferably, however, the monitoring means includes means for monitoring the voltage across the electrical circuit. It is found that at resonance the monitored voltage will dip and this is relatively easy to detect.

The invention is particularly suited for use in a biosensor and particular applications will be described below. This is because the body can be physically separate from the inducing means. Thus, the body can be placed into a container such as a microtiter plate or the like while the inducing means is positioned underneath the plate. This is particularly advantageous since no electrical connections need to be made to the body within the plate.

In order to implement the acoustic monitor in a biosensor some means is necessary to attract the relevant microbes or other material to the body within the liquid. This could be achieved by suitably coating the surface of the body to attract the relevant microbes, typically by using suitable antibodies, but preferably is achieved by using macromolecules, such as antibodies or lectins or other affinity-based molecules, natural or synthetic, to specifically bind the cells of interest. These. macromolecules will be labeled with ferrimagnetic or magnetized particles of controlled-size encapsulated nanocrystals. The preferred embodiment of the magnetized microparticles, including ferromagnetic iron oxide magnetite ($Fe_3O_4$), are magnetosomes, or ferritin (or magnetoferritin) or any other iron-containing biological macromolecule or supramolecular protein cages, natural or synthetic, that may be affected by a magnetic pull such as from a samarium-cobalt magnet (Sm—Co) or NdFeB. In addition, when the technology will allow it, chemically synthesized ultra fine magnetic particles in the nanometers range may be used to which polymer modification will allow for ligand binding.

Magnetically-labeled antibodies will be made specific for the microbe of interest, which implies that the user must know in advance what he is testing for, as is usually the case in all diagnostic immunoassays. The conjugated antibodies will typically be available in sealed, sterile 1 ml plastic containers, wherein the sample will be placed. These antibodies will bind to the cells, in effect coating them, if there is a specific molecular recognition mechanism involved. The magnetically-coated cells will be removed from the bulk solution by a magnetic pull, thereby providing in effect a purification step, toward the magnetic pole. At the same time, these same cells are drawn towards the sensing surface, also present in the plastic container. This ensures the microbial reader responds quickly to the cells of interest. This will cause a change in the mass of the body and hence a change in its resonance frequency which is then monitored to obtain information about the number of microbes in the sample.

The acoustic monitor can be constituted as a hand-held microbial cell counter and is based on a new concept that has never been applied to sensor related problems and thus provides strong competitive advantages that build on the technical merits of the new glass disc sensing technology, finally satisfying the key needs of a hand-held reader. For example, the body, such as a glass disc and metal coating can be disposable and thus constitute one of the simplest and cheapest disposables of its type. The cost effectiveness of this disposable measurement cell is likely to lead to new markets, Particularly for microbial screening activities where large numbers of measurements are made. Further, the coated disc does not require the use of specialized surface chemistry to localize the microbes to the sensor, instead, for example ferritin antibodies, "grab" the relevant microbes during mixing and the magnetic field quickly transports the conjugate direct to the sensor surface.

DETAILED DESCRIPTION

Some examples of acoustic biosensors according to the invention, will now be described with reference to the accompanying drawings.

Figure 1:
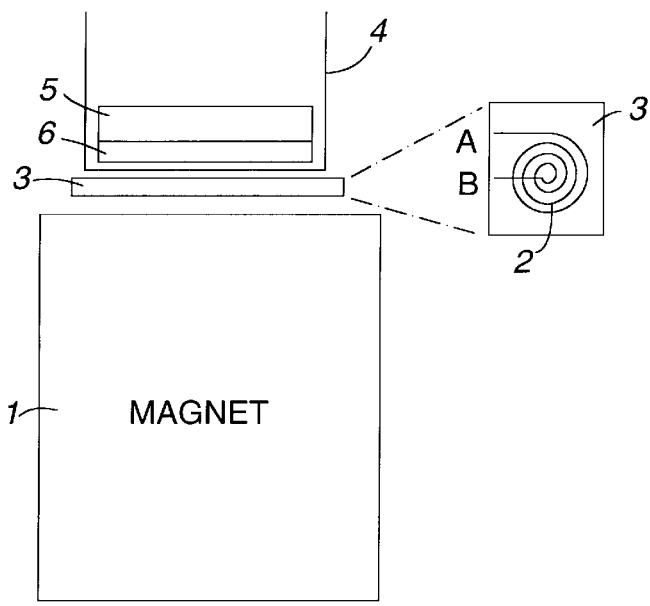
FIG. 1 is a schematic side view of the main components of one example of a biosensor with the processing components omitted.

The biosensor shown in FIG. 1 comprises a permanent magnet 1 Above the magnet 1 is positioned an electrical coil 2 which is provided on a support 3. The coil is normally wound from enameled copper wire to form a flat spiral. To function efficiently, the coil should have 20 or more turns, preferably 30 to 50 spiral turns (for clarity only a few turns are shown in FIG. 1), and maintain an electrical resistance that is as low as possible. Copper wire 85 to 125 $\mu$m thick is most suitable for this. The coil is positioned just under a container 4, preferably having a thin base less than 1 mm thick, which will include a liquid which is to be analyzed or assayed. Within the container 4 is positioned a glass disc 5 having a diameter for example in the range 10–13 mm, and a thickness of about 500 microns. On the underside of the disc 5 is provided a metallic or other conductive coating 6, preferably aluminium, with a thickness of about 1 micron, and preferably of low density. Ideally, the disc should not vary in thickness across its width and should be free of any internal fractures of the glassy medium. In addition, the thickness of the disc should not vary with changes in temperature, which is best achieved with silica glass, particularly as this material exhibits one of the lowest expansion coefficients known. More recently, a zero coefficient glass material has become available, which will further enhance the detection of small numbers of cells.

The magnet 1 is preferably made from NdFeB material which provides for a permanent magnet the most intense fields and which has the consequence of facilitating maximum excitation of the glass disc 5. The magnet 1 can vary greatly in size although sizes between 25×25×50 mm and 12×12×10 mm are typical. At the pole face these magnets provide a useful 1 Tesla magnetic field suitable for excitation of the phenomena of interest. Longer magnets have the additional advantage of providing fields that extend for greater distances beyond the pole face, which means the magnet can be located further away from the sensing disc, without compromising excitation.

Figure 2A:
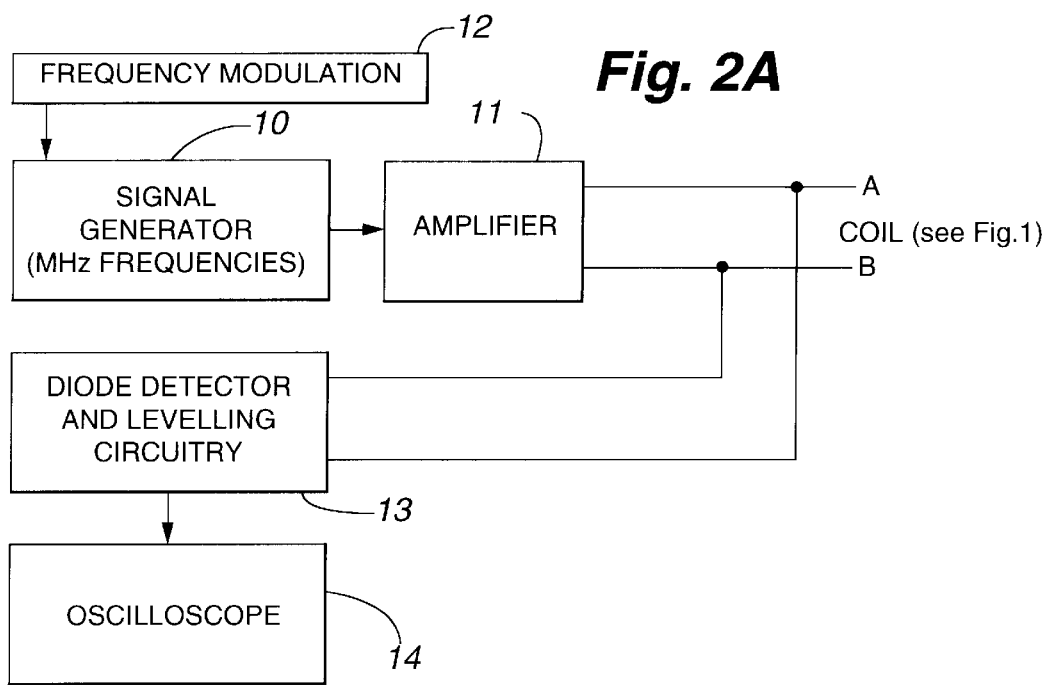
FIG. 2A illustrates one example of processing components for use with the FIG. 1 example.

FIG. 2A illustrates one example of a circuit for connection to the terminals A,B of the coil 2. The circuit comprises a signal generator 10 for generating an AC current (in the MHz band) which is fed to an amplifier 11 and then to the coil 2. The signal generator 10 is connected to a frequency modulation device 12 to enable, the oscillation frequency to be varied.

The voltage across the coil terminals. A, B is monitored by a diode detector and leveling circuitry 13 whose output is displayed on an oscilloscope 14. An example of that output is shown at 15 in FIG. 2B where the Y axis is the voltage detected across A, B and the X axis is the AC frequency.

In use, a liquid to be analyzed is provided in the container 4 along with ferritin labeled antibodies. Ferritin labeled antibodies are antibodies that adhere to the microbe of interest, however they differ by a small chemical modification that adds a ferritin particle, some 50 Å in diameter. The function of the ferritin particles is to move toward the magnetic pole, while at the same time drawing the attached microbes in the same direction. This ensures the microbial reader responds quickly to the cells of interest. Thus, cells recognized by the ferritin labeled antibodies are magnetically driven to the glass disc surface thereby varying the mass of the glass disc. In general antibodies labeled with any magnetic particle that are less than 2000 Å in diameter are suitable.

Figure 2B:
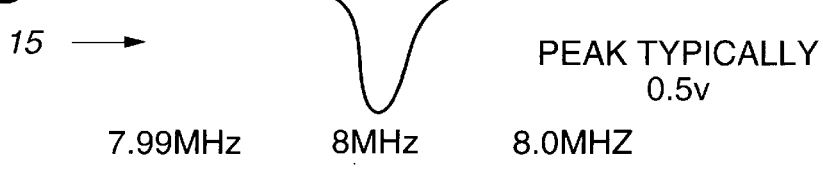
FIG. 2B illustrates a typical oscilloscope display.

An oscillating current passing through the coil 2 will induce oscillating eddy currents in the metal coating 6. The eddy currents interact with the magnetic field generated by the magnet 1 so that a force is applied to the metal coating. This force oscillates so that the metal coating is vibrated and the thickness of the coating is such (similar to the skin depth) that the oscillating shear wave is coupled into the glass disc 5 which is thus also caused to vibrate and to resonate, typically in the range 5–40 MHz, depending on its thickness. By varying the oscillation frequency using the frequency modulation device 12, it is possible to achieve a resonant condition of the glass disc 5 and metal coating 6 and this is seen on the oscilloscope 14 by a dip in the voltage across the coil. The voltage across the coil corresponds to the sum of the input voltage and the voltage induced in the coil by the eddy currents. At resonance, this induced voltage will be out of phase with the input voltage thus causing a small decrease in the monitored voltage, as shown in FIG. 2B.

If the mass of the body constituted by the glass disc 5 and the metal coating 6 changes, then the resonant frequency will change and this will be detected by a change in the position of the dip.

At resonance, the thickness of the glass disc 5 and metal coating 6 together will be about $n\lambda/2$ where n is an integer and $\lambda$ is the wavelength of the shear wave in the disc.

In summary the apparatus operates as follows:

a) Electrons are forced to move in the conductive surface 6 of the disc 5, due to the electromagnetic field radiating from the planar coil 2.

b) A magnetic field that is arranged to be perpendicular to the motion of these electrons, elicits a sideways force that transfers motion directly to the metal ions.

c) Because of the shape of the coil 2, the sideways force acts like an expanding and contracting starburst, exciting the surface and generating ultrasonic waves.

d) The ultrasonic waves are hundreds of microns long and travel away from and perpendicular to the metal surface 6, with a shear horizontal polarization.

e) At specific frequencies, superposition of the wave reflected from the upper surface and the wave generated from the lower surface, induce an acoustic wave that is stationary between the disc faces.

f) At these specific frequencies, the increased motion of the lower surface of the disc 5, in the presence of the magnetic field, induces an additional current in the metal surface and a further voltage across the coil.

g) If a sub-micron layer of material is deposited on the disc then all of the standing wave resonances reduce slightly in frequency.

h) If a liquid is added to the vibrating surface, the resonance frequencies drop, and a more viscous solution induces even greater reductions in frequency.

i) If cells are present in the liquid they will diffuse and bind to the disc surface, again reducing the resonance frequency in proportion to quantity.

j) To identify the presence of specific cell types, cell surface antibodies that are coordinated with ferritin particles are pre-mixed with the test solution, adhering only to the cells of interest.

k) As a consequence, the cells that are coordinated with ferritin particles are quickly accelerated to the disc surface, due to the attractive influence of the DC magnetic field.

The principle of operation of the glass disc is as follows:
If the coil is energized with a current at the standing wave resonance frequency given $$F_n = \frac{nV_s}{2t}$$

where $V_s$ is the shear acoustic velocity, n is the order of the mode and t is the thickness of the disc, then shear acoustic standing waves form between the upper and lower surfaces. FIGS. 5A–5D show a much exaggerated sideways displacement of the motive interior of the glass disc, corresponding to the first four shear acoustic modes and including the fundamental standing wave vibration of the plate (n=1). Of note in these vibrations is the characteristic movement of both free surfaces and the alternate symmetry and asymmetry of the modes. Note that the movement of the disc is extremely small and never apparent, unless optical interferometric equipment is focused onto the edge of the disc. Even the displacements are particularly difficult to monitor.

The amplitude of the excitation effect can be controlled by using the following equations which relate aspects of the coil and the magnet to the level of the detected signal.

$$Z = F_{mag}^2 F_{elect} K_{res} \left( \frac{B^2 N^2 A}{Z_s} \right)$$

$$F_{elect} = \exp\left( -\frac{4\pi d_e}{R_e} \right)$$

$$F_{mag} = 1 - \left( \frac{2d_m}{D_m} \right)$$

$$V = IZ$$

Where Z is the electromagnetic to acoustic transduction efficiency, $K_{res}$ is an amplification factor due to the resonance, B is the DC magnetic field, N is the number of wire turns of the electrode, A is the area of the electrode and $Z_s$ is the acoustic shear impedance of the metal surface concerned. Separation parameters are Felect, which depends on $d_e$, the electrode separation, and $R_e$, the electrode diameter, also $F_{mag}$, which depends on $d_m$, the magnet separation, and $D_m$, the pole diameter. Finally, V is the resulting voltage across the receiver terminals, according to the electrode current I.

The thickness of the metal film 6, which coats the glass disc 5, is also crucial. Ideally, this is kept as thin as possible in order to minimize any effect it may have on the thermally stable characteristics of the glass. In addition, the maximum useable frequency of the disc is limited by the thickness of the film according to $$t_r = [1 + (\pi\sqrt{2}\ ft/V_s)^4]^{-1}$$

where $t_r$ is a film efficiency factor and f is the operating frequency. From that it is clear that the thin film conductors have different excitation characteristics from solid conductors, which has the advantage of a higher frequency of operation. These higher frequencies of operation are generally preferable as the sensitivity to surface microbes increases too. Additionally, the damping of the resonance that occurs for low frequency resonances can sometimes be reduced at higher frequencies, therefore the sensing characteristics of the cell reader are improved all round.

The change in resonant condition with mass of the disc can be used to achieve various biological monitoring processes. For example, using the FIG. 2A circuit, the system can be set up so that it is in resonance and then the system can be left while a biological process takes place which may or may not result in mass being deposited on the glass disc. If mass is deposited then the resonant frequency will decrease and this can be found since the frequency modulation device 12 will sweep the oscillation frequency over a range of say a few kHz and the oscilloscope will display the new resonance frequency. Alternatively, in a variation of FIG. 2A without frequency modulation, the signal generator can be set at a fixed resonance frequency. Any change as a biological process occurs will reduce the amplitude of the dip.

Figure 3A:
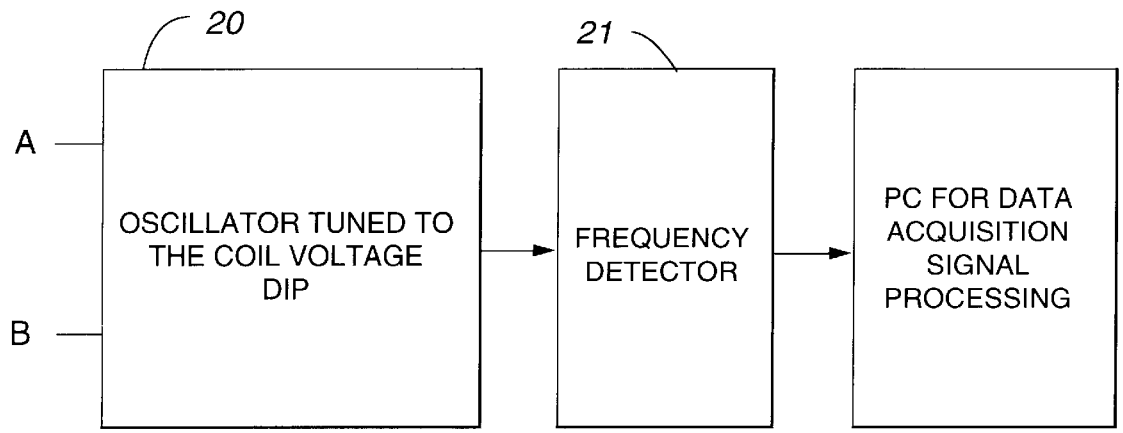
FIGS. 3A and 3B illustrate a second example of processing components for use with the FIG. 1 example.
Figure 3B:
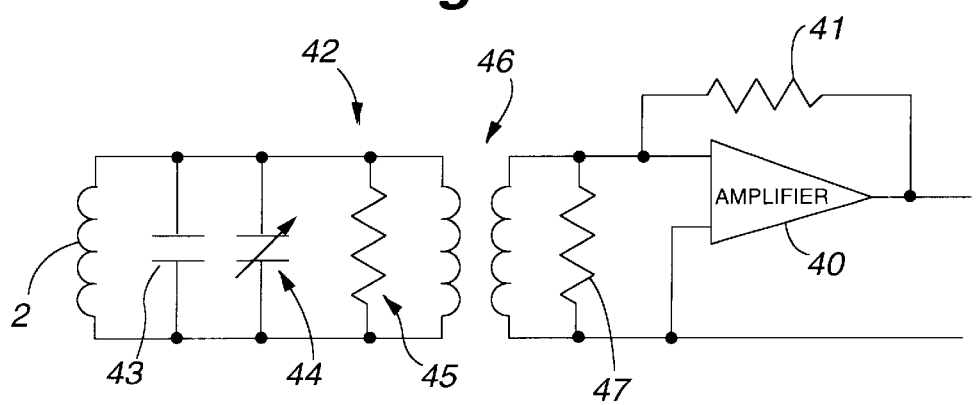

FIGS. 3A and 3B illustrate an alternative circuit. In this case, a marginal oscillator 20 is connected to the terminals A,B of the coil 2, the oscillator 20 being of a conventional type (shown in FIG. 3B) which responds to a resonant impedance condition and maintains that condition by varying the oscillation frequency as necessary. This oscillation frequency can be detected by a detector 21 connected to the source 20, the output from the detector being fed to a PC which can store the results allowing an operator subsequently to monitor the process.

The oscillator circuit 20 is shown in more detail in FIG. 3B. The circuit includes an amplifying component 40, usually an rf mosfet device, with amplifier feedback via a resistor 41. A circuit 42 determines the frequency of the oscillator. The circuit 42 includes the coil 2 which has an inherent capacitance indicated at 43. The coil 2 is connected to a variable capacitor 44 for tuning purposes, a resistor 45 and a transformer 46. A resistor 47 is connected across the transformer 46 and the terminals of the transformer are connected to the inputs of the amplifying component 40. The output of the oscillator is then connected to the frequency detector 21, as shown in FIG. 3A.

Any change in impedance caused by a change in the mass of the body will be in the opposite sense to that required by the amplifier 40 and so the impedance change is inverted by the transformer 46. This arrangement then allows the acoustic resonance to determine the frequency of the marginal oscillator.

In a modified arrangement (not shown), the coil 2 could be provided in series with a capacitor connected directly to the amplifying component 40 and the circuit of FIG. 3B would then not be needed.

Figure 4:
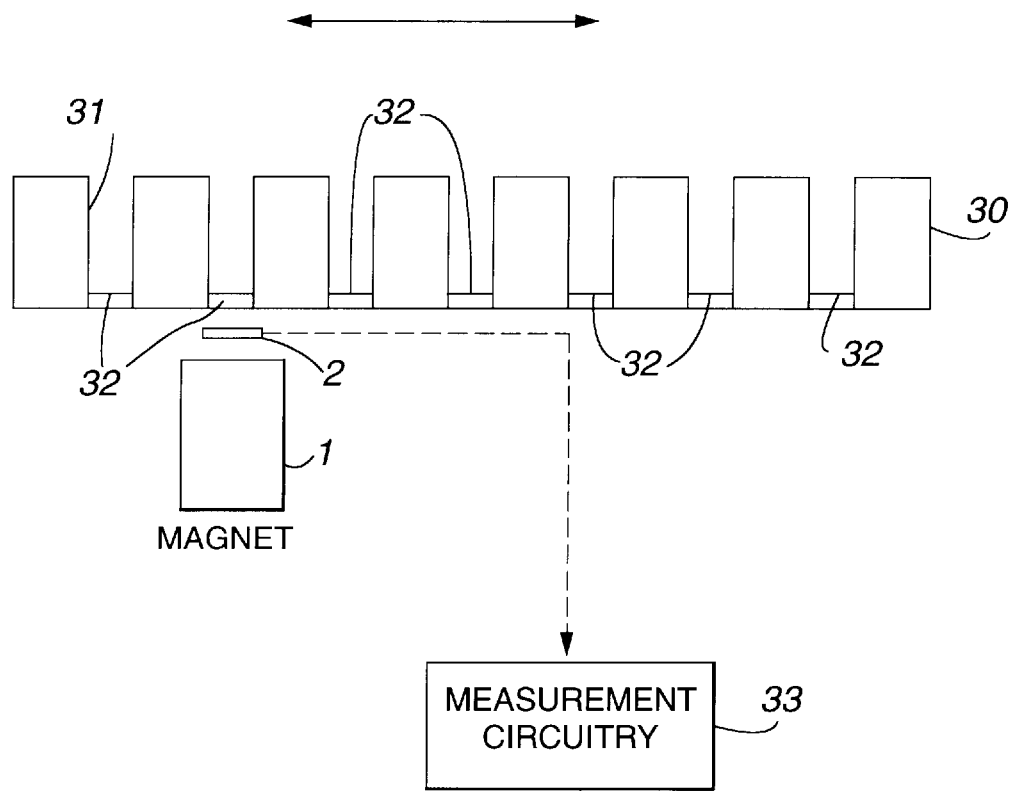
FIG. 4 illustrates a second example of a biosensor.
Figure 5A:
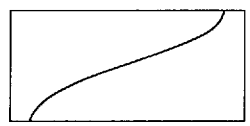
FIGS. 5A–5D illustrate schematically the sideways displacement of the glass disc corresponding to the first four shear acoustic modes respectively.
Figure 5B:
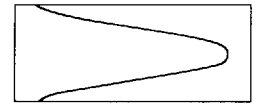
Figure 5C:
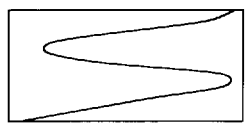
Figure 5D:

FIG. 4 illustrates an alternative example in which a multiple assay in a microtiter plate 30 can be monitored. Each well 31 of the microtiter plate 30 has a body 32 comprising a glass disc 5 and metal coating 6 similar to that shown in FIG. 1. Beneath the microtiter plate 30 and mounted on a stand (not shown) is the magnet 1 and coil 2 of different size. The measurement circuitry attached to the coil 2 is shown schematically at 33 and will be similar to either that shown in FIG. 2 or FIG. 3. In this case, the microtiter plate 30 can be indexed in steps over the coil 2 and after each step the resonant condition of the body 32 of the appropriate well can be. monitored so that the process taking place in each well can be monitored. Some examples of the applications of this new biosensor are described below.

1. In vitro susceptibility acoustic antimicrobial (for example antifungal or antibacterial) screening device. In order to detect the fungistatic or fungicidal effects of various natural plant extracts or synthetic molecules, yeast cells are immobilized on glass discs and are allowed to grow at optimal conditions except for their exposure to various quantities of the aforementioned extracts. If these extracts have any effect then yeast will not grow and this can be monitored using acoustic waves. The non-growth and plasmokinetics of a drug being studied will be detected if the monitored resonant frequency does not change.

2. Immunoassay of bacteria/yeast/unicellular algae. An immunoassay can be developed whereby a layer of antimicrobial (bacteria/yeast) outer-membrane or cell wall immunoglobulin molecules are attached to the glass disc (or even glycoproteins—specific to microbial outer-membranes) and the assembly will detect the increase in mass caused by the addition of the sample to be analyzed that may contain microbes. This could be achieved using the circuit of either FIG. 2 or FIG. 3 and monitoring the decrease in resonant frequency. Also, an antigen or antibody immunoassay could be developed for diagnostic purposes of physiological fluids (serum, saliva, mucosal fluids) or environmental fluids such as waste water.

3. A pollution assay for layers of yeast, bacteria, unicellular algae by exposing them to various polluted (or contaminated) aqueous solutions and monitoring for toxicity effects shown by the lack of growth detected by a constant resonant frequency.

4. The biosensor shown in FIG. 4 could be used in a mammalian cell growth monitoring system to indicate cell growth/coverage after seeding the microtiter wells with cells. Titer wells incorporating mass sensitive discs would indicate the presence or lack of cell growth corresponding to a change or no change in resonant frequency. In addition, toxic substances such as toxins (including mycotoxins), pesticides, alkaloides, viruses, growth or mutagenic factors could be determined because of their effect on the rate of cell growth or cell killing. The well-sized glass discs will be covered with a transparent metal coating of indium tin oxide, itself covered with a cell binding material such as polylysine but not restricted to this. These discs are introduced into each cell well, sterilized using gamma-rays, ready to allow cell growth. Transparency allows the scientist to check in the microscope for cell morphology.

A widespread problem with existing biosensors is the absorption of unwanted components to the surface of the mass sensitive acoustic sensor. An approach for removing this problem could involve significantly reducing the area of the sensing surface relative to areas which have high analyte specificity Another approach would be to add a synthetic polymer which would reduce non-specific binding. The present invention can address this problem as acoustic waves can be generated in any microscopic conductive structures. Either micron sized metal spheres or chemical conjugates comprising nanometer sized metal particles Further competitive advantages ensue from the manufacturability of the handheld reader. The solid state components, disc, coil, magnet and oscillator have few parts, reducing the likelihood of failure during service. In addition there is little or no need for any stringent mechanical alignments. For example, there are no exacting tolerances on thickness of the glass disc, or the thickness of the metal coating, hence a dimensional variability of 2% would be more than satisfactory. In particular, the disc can be located within the hand-held reader with horizontal variability of approximately 10% of the disc diameter, which is superior to acoustic or optical biosensors. In addition, as long as the excitation signal is detectable, vertical positioning of the disc does not interfere with performing a cell count. In summary, the excitation signal depends only on the mechanical properties of the disc and since the disc has no rigid contact to the reader the only variable is the surface chemistry, significantly increasing the signal to noise ratio of the microbe measurement.

We claim:

1. An acoustic monitor assembly for monitoring the magnetic particulate and magnetically-labelled content of a liquid comprising,
   a body having an electrically conductive portion, the body contacting a liquid whose content is to be monitored in use,
   a magnetic field generator for generating a magnetic field to which the electrically conductive portion of the body is exposed, the magnetic field generator being positioned such that magnetic particulates in the liquid are drawn on to said body,
   means for inducing eddy currents which oscillate at an acoustic frequency in the electrically conductive portion of the body and in response to which the body is caused to vibrate at an acoustic frequency, and
   means for monitoring the vibration condition of the body so as to provide an indication of the content of said particulates which are drawn onto said body in the liquid.

2. An assembly according to claim 1, wherein the body comprises a mass carrying a metal coating.

3. An assembly according to claim 2, wherein the thermal expansion co-efficient of the mass is less than that of the metal coating.

4. An assembly according to claim 2, wherein the mass comprises silica glass.

5. An assembly according to claim 2, wherein the thickness of the metal coating is substantially equal to the skin depth of the electrically conductive portion.

6. An assembly according to claim 1, wherein the magnetic field generator comprises a permanent magnet.

7. An assembly according to claim 1, wherein the magnetic field generator generates a magnetic field of about one Tesla.

8. An assembly according to claim 1, wherein the inducing means comprises an electrical circuit and means for passing at an oscillation frequency through the circuit.

9. An assembly according to claim 8, wherein the electrical circuit includes an electrical coil.

10. An assembly according to claim 8, wherein the means for passing an oscillating current through the circuit includes means for varying said oscillation frequency.

11. An assembly according to claim 10, wherein the electrical circuit includes an electrical coil and wherein said oscillation frequency depends on the electrical impedance of the coil.

12. An assembly to claim 8, wherein the monitoring means monitors the voltage across the circuit.

13. An assembly according to claim 1, wherein the monitoring means is adapted to monitor and indicate a resonant condition of the body.

14. An assembly according to claim 13, wherein the eddy current inducing means comprises,
   means including an electrical circuit for passing an oscillating current at an oscillation frequency through the circuit; wherein the means for passing an oscillating current through the circuit includes,
   means for varying said oscillation frequency and wherein the means for passing an oscillating current through the circuit is responsive to the monitoring means to vary the oscillation frequency to maintain the body in a resonant condition.

15. A biosensor including an acoustic monitor assembly according to claim 1.

16. A biosensor comprising an acoustic monitor assembly according to claim 1, wherein the acoustic monitor assembly includes, a plurality of assay containers for holding a plurality of liquid samples, and a plurality of bodies each having an electrically conductive portion, each body being positioned in a respective assay container, and wherein the plurality of said assay containers are movable relative to the magnetic field generator and monitoring means of the acoustic monitor assembly to enable the vibration condition of each body to be monitored.

17. A method of counting microbial cells in a liquid using a biosensor according to claim 15, the method comprising mixing ferrimagnetic or magnetized particles in the liquid, the particles having an affinity for the cells to be counted; activating the inducing means and magnetic field generator whereby the particles are drawn toward the body of the biosensor; and determining from information supplied by the monitoring means, a microbial cell count.

18. A method according to claim 17, wherein the particles comprise magnetosomes.

* * * * *